(12) United States Patent
Hall-Puzzio et al.

(10) Patent No.: US 6,531,119 B1
(45) Date of Patent: Mar. 11, 2003

(54) COMPOSITIONS WITH LOW IRRITANCY

(75) Inventors: Patricia Ann Hall-Puzzio, Succasunna, NJ (US); Anne Elisabeth Vickery Gale, Landing, NJ (US)

(73) Assignee: Colgate-Palmolive Company, New York, NY (US)

( * ) Notice: Subject to any disclaimer, the term of this patent is extended or adjusted under 35 U.S.C. 154(b) by 0 days.

(21) Appl. No.: 09/593,853

(22) Filed: Jun. 14, 2000

Related U.S. Application Data

(63) Continuation-in-part of application No. 09/035,483, filed on Mar. 5, 1998, now abandoned.

(51) Int. Cl.[7] .............................. A61K 7/32; A61K 7/00
(52) U.S. Cl. ........................................ 424/65; 424/401
(58) Field of Search .................................. 424/65, 401

(56) References Cited

U.S. PATENT DOCUMENTS

| | | | | |
|---|---|---|---|---|
| 4,164,564 A | * | 8/1979 | Chen ........................... | 424/83 |
| 4,233,192 A | * | 11/1980 | Iindemann et al. ......... | 252/545 |
| 4,322,545 A | * | 3/1982 | Scala, Jr. .................... | 560/103 |
| 5,462,691 A | * | 10/1995 | Shimada et al. ....... | 252/174.15 |
| 5,605,681 A | * | 2/1997 | Trandai et al. ................ | 424/65 |
| 5,730,963 A | * | 3/1998 | Hilliard, Jr. et al. .......... | 424/65 |
| 5,976,555 A | * | 11/1999 | Liu et al. .................... | 424/401 |
| 6,010,991 A | * | 1/2000 | Dabestani ................... | 510/139 |

FOREIGN PATENT DOCUMENTS

| | | |
|---|---|---|
| EP | 0013390 | 7/1980 |
| EP | 0590601 A2 | 4/1994 |
| EP | 0623338 A2 | 11/1994 |
| JP | 07179331 | 7/1995 |
| WO | WO 94/24997 | 11/1994 |
| WO | WO 99/44576 | 9/1999 |
| WO | WO 99/44577 | 9/1999 |

OTHER PUBLICATIONS

Article on: "Using Fatty Acid Esters in Cosmetics" from *Manufacturing Chemist*, Jan. 1996, pp. 34–35.

* cited by examiner

*Primary Examiner*—Thurman K. Page
*Assistant Examiner*—S. Tran
(74) *Attorney, Agent, or Firm*—Rosemary M. Miano

(57) ABSTRACT

The present invention utilizes a polyethylene glycol diisostearate having an average degree of ethoxylation of from 40–100 as a component of a soap-based gel composition suitable for use in formulating stable cosmetic compositions, especially low irritancy deodorants.

24 Claims, No Drawings

COMPOSITIONS WITH LOW IRRITANCY

This case is a continuation-in-part of U.S. Ser. No. 09/035,483 filed on Mar. 5, 1998 now abandoned.

FIELD OF THE INVENTION

The present invention is directed to cosmetic compositions such as deodorants and antiperspirants which are based on soap gelled systems and which have reduced irritancy when applied to skin. The composition may be in the form of a gel, stick, soft solid or cream. The present invention is directed to clear, translucent and opaque products, especially clear cosmetic (for example, deodorant) gel compositions and, more especially, a soft gel or stick composition gelled utilizing a soap gelling agent, having reduced skin irritation potential yet having improved clarity.

BACKGROUND OF THE INVENTION

Gel compositions, such as soap-gelled compositions, have proven to be a convenient and efficient vehicle for the application of various active ingredients to the skin. Such active ingredients include (but are not limited to) antiperspirants, deodorants, perfumes, sunscreens, cosmetics, emollients, insect repellents, medicaments and the like. Such gel compositions may be in the form of a gel, soft solid, cream and/or a stick. Rubbing such a product containing an appropriate amount of active ingredient dissolved or dispersed therein against the skin causes transfer of a film of the composition to the skin surface against which the soft gel or stick is rubbed, leaving the active ingredient within the film of the composition on a desired skin surface area.

Conventional soap-gelled base formulations (that is, base gel compositions gelled using a soap gelling agent) for depositing the active ingredient normally include as major components a mixture of from about 3 to about 10% by weight, of the total weight of the composition, of an alkali metal salt of a fatty acid containing primarily 12 to 22 carbon atoms, for example, sodium stearate or sodium palmitate soap, and a suitable solvent in which the soap is soluble, for example, water, organic solvents such as lower monohydric alcohols and/or glycols, or mixtures thereof. The product forms described above (sticks, gels, soft solids, creams) may be formulated as known in the art, depending, for example, on the amount of gelling agent utilized. For example, the stick is formed by pouring a mixture of the various components into a suitably shaped mold and permitting the composition to gel and cool, thereby hardening the composition.

A typical example of a water-based cosmetic stick formulation is disclosed in U.S. Pat. No. 4,322,400 to Yuhas, wherein the composition includes a mixture of water, sodium stearate, a cosmetically active ingredient and up to about 5% by weight, of the total weight of the composition, of sodium chloride, which tends to increase the setting point of the gel. The composition may also optionally contain up to about 10% by weight of one or more glycols, such as propylene glycol or polypropylene glycols having molecular weights of up to 25,000.

Other gel stick formulations, which are essentially free of water, are disclosed, for example, in U.S. Pat. No. 5,284,649 to Juneja. The composition of this patent includes a mixture of about 1–20% by weight, of the total weight of the composition, of a fatty acid soap, a zinc pyridinethione as a deodorant active, and about 7–95% by weight, of the total weight of the composition, of a polar solvent system which solubilizes the soap. Suitable solvents in the polar solvent system include lower monohydric alcohols such as ethanol or propanol, glycols such as ethylene glycol and propylene glycol, and polypropylene glycols such as dipropylene glycol, tripropylene glycol and higher glycols.

In addition, U.S. Pat. No. 4,504,465 to Sampson, et al discloses a water-free stick formulation based on a mixture of about 3–10% by weight soap, from about 6–70% by weight of an aliphatic polyhydric alcohol containing 2 or 3 carbon atoms and from 2 to 3 hydroxy groups, for example, ethylene glycol, propylene glycol, trimethylene glycol or glycerine, and from about 20 to 80% by weight of a condensation product of the formula $R(OC_3H_6)_a(OC_2H_4)_bOH$, wherein R is either hydrogen or a hydrocarbon chain having from about 2–20 carbon atoms and a and b are each from 0 to 35 and a+b is from 5 to 35. The preferred solvent system disclosed includes a mixture of a lower alkanol such as ethanol, propylene glycol and a major amount of polypropylene glycol, polyethylene glycol or condensates of propylene oxide with $C_2$–$C_{20}$ alcohols.

European Patent Application (EP) 284765 B1 discloses a soap-based cosmetic stick formulation of improved transparency and of more pleasing aesthetic appearance, wherein the solvent used to formulate the stick is dipropylene glycol or a mixture of dipropylene glycol and propylene glycol.

A non-soap-based stick antiperspirant formulation is disclosed in U.S. Pat. No. 5,200,174 to Gardlik, et al, wherein the solvent system includes a mixture of 2-oxazolidinone and one or more hydroxy solvents inclusive of lower alkanols, glycols such as propylene glycol and polyglycols such as polyethylene and polypropylene glycols. Dipropylene glycol and combinations of dipropylene glycol and propylene glycol are specifically used in the examples.

Gel stick formulations containing both a glycol and water are also known. For example, U.S. Pat. No. 4,702,916 to Geria discloses an analgesic stick composition including a mixture of from about 10–65% by weight of an alcohol, about 6–10% by weight soap and about 10–30% by weight water. The alcohol component preferably is propylene glycol.

One of the problems associated with the use of soap-based products is that they may be harsh to the skin of some consumers, causing skin irritation and leading to the development of erythema. Substitution of the soap with other gelling agents such as dibenzylidene alditol as in U.S. Pat. No. 5,200,174, discussed above, may reduce the irritation problem, but these formulations present stability problems and add to the expense of the product.

Japanese Patent Document No. 63-270614 discloses a soap-free gel base including a mixture of 0.1–5% by weight of a carboxyvinyl polymer used as a gelling agent, 30–80% by weight of a polyhydric alcohol and water. Examples of the disclosed polyhydric alcohols include propylene glycol, 1,3-butylene glycol, dipropylene glycol, tripropylene glycol and hexylene glycol. This composition is described as being safe to the skin.

A stick composition also disclosed as having a reduced tendency to irritate skin, while also being transparent, is disclosed in U.S. Pat. No. 5,128,123 to Brewster. This composition includes, in addition to soap and a polyhydric alcohol solvent such as propylene glycol, up to 40% by weight of an alkoxylate copolymer which is a condensate of ethylene oxide and propylene oxide, or an addition product condensate of ethylene oxide and propylene oxide with ethylene diamine.

A co-pending case now issued as U.S. Pat. 5,730,963 to the same owner as this application describes an approach suitable for use with soap-based and non-soap-based gelling systems which comprises the use of selected higher molecular weight glycols. This case recites lower irritation.

U.S. Pat. 6,036,964, now issued to the same owner as this application, describes a personal care product with an enhanced delivery system comprising a multi-component glycol system with at least three different components (for example, propylene glycol, dipropylene glycol and tripropylene glycol) in selected amounts.

Irritation may, in fact, be a cumulative result of a number of ingredients. The conventional wisdom up to now, for producing cosmetic formulations which are milder to the skin, appears to be (a) elimination of soap totally from the formulation and replacing it with a non-soap gelling agent, (b) reducing the amount of soap present in the formulation and including a different, less irritating co-structurant such as alkylene oxide condensates, or (c) eliminating both the soap and irritating lower alcohols, such as ethanol, from the formulation. Efforts to find additives for reducing irritation have not always proven successful because of stability problems.

The search for improved products not only includes those having reduced irritancy, it also includes the search for products having other desirable properties and the flexibility to achieve more than one goal.

Recently, in view of widespread consumer appeal, much effort has been expended for providing, for example, clear gel compositions, such as clear stick or soft gel compositions, which retain clarity over an extended period of time (that is, has a stable clarity) so as to have a long shelf life. A particular problem in gel compositions, for providing a clear composition, is avoiding crystals forming in the composition during, for example, the shelf life and until the product has been used up by the consumer.

The aforementioned U.S. Pat. No. 5,128,123 discloses cosmetic stick compositions which are not only milder but which are also clear, having the above-referred-to alkoxylate copolymer and, additionally, a basic amine clarifying agent; this patent further discloses that the clarifying agent is preferably selected from amino alkanols having from 2–6 hydroxyl groups, particularly effective being the propanol amines.

U.S. Pat. No. 5,128,123 also defines what is meant by the term "clear" with respect to the stick composition described therein. Specifically, the term "clear" has its usual dictionary definition; thus, a clear stick, like glass, allows for ready viewing of objects behind it. This patent contrasts clear sticks with translucent sticks, which allow light to pass through but causes the light to be so scattered that it will be impossible to clearly identify objects behind the translucent stick. This patent also shows that, in the present art, there is a difference between clear, translucent and opaque sticks; this patent goes on to define clear, translucent and opaque sticks based on transmittance of light of wavelengths in the range of 400 to 900 nm through a sample 1 cm thick.

U.S. Pat. Application Ser. No. 08/054,302 to Kasat, now issued as U.S. Pat. No. 5,458,880, the contents of which are incorporated herein by reference in their entirety, discloses that by incorporating a sodium salt of a methyl carboxy derivative of ethoxylated lauryl alcohol (for example, sodium laureth-13 carboxylate as defined in the *CTFA International Cosmetic Ingredient Dictionary* (4th Ed. 1991)) in a soap-gelled stick composition, a transparent, clear stick, which maintains such transparency and clarity for extended periods of time, can be achieved.

U.S. Pat. No. 5,424,070 to Kasat, et al, the contents of which are incorporated herein by reference in their entirety, discloses that by incorporating an Eumulgin compound (for example, Eumulgin L, which is PPG-2-Ceteareth-9, as defined in the aforementioned *CTFA International Cosmetic Ingredient Dictionary*) in a soap-gelled stick composition, a transparent, clear stick which maintains such transparency and clarity for extended periods of time can be achieved.

Neither of U.S. Pat. No. 5,458,880 nor U.S. Pat. No. 5,424,070 focus on reduction of skin irritation potential.

Notwithstanding the foregoing, it is still desired to provide a cosmetic gel composition, such as a deodorant gel composition, which can be in the form of a soft gel, soft solid, cream or hard stick, and which has reduced skin irritation potential. It is further desired to provide such composition, which is clear and which maintains such clarity over extended periods of time.

Accordingly, it is a first object of the present invention to provide cosmetic compositions which contain a soap-based gelling system and which have a reduced skin irritation potential.

It is a further object of the invention to provide a choice of various cosmetic products (that is, products which can be used as a vehicle for applying a cosmetically active ingredient, for example an antiperspirant active or fragrance) to the skin), which can be clear, translucent or opaque and which can have form of solid, cream, gel, soft solid, etc. and which have reduced skin irritation potential.

It is another object of the present invention to provide a base composition, which can take the form of a solid, cream, gel, soft solid, etc. in which a cosmetically active ingredient can be incorporated to provide a cosmetic gel composition, having a soap gelling agent and which has reduced skin irritation potential even if glycols are included in the formulation.

It is a still further object of the present invention to provide a cosmetic composition, gelled, for example, by a soap gelling agent, and having glycols and cosmetically active ingredients (for example, a deodorant active ingredient) incorporated therein, which has reduced skin irritation potential.

It is a still further object of selected embodiments of the present invention to provide a deodorant composition, especially in the form of a soft gel or stick, containing glycols, having reduced skin irritation potential.

SUMMARY OF THE INVENTION

The present invention comprises the use of a polyethylene glycol diisostearate having an average degree of ethoxylation of from 40–100 as a component of a soap-based gel composition, which diisostearate is suitable for use in formulating stable cosmetic compositions, especially as antiperspirants and/or deodorants, and which diisostearate is compatible with such formulations. The use of the diisostearate reduces the irritancy of the compositions.

DETAILED DESCRIPTION OF THE INVENTION

The polyethylene glycol diisostearates useful in this invention have an average degree of ethoxylation of from 40–100, especially 80–100, and most particularly 90. Mixtures of such diisostearate can also be used. This component should be added to the composition in an amount sufficient to reduce irritation. While various ranges are possible, such as 0.05–5% and 0.1–10%, it is believed that for aesthetic reasons the upper limit can be about 40% by weight based on the total weight of the composition. While the broad range would be 0.05–40%, more particular ranges include 1.0–30%, and 1.0–20%, especially 1–10% and, more especially, 1.0–5.0% by weight based on the total weight of the final cosmetic composition. Particular addition levels include, for example, from 1.0–2.5% and especially 2.0%. While it is not known why these components have a low irritancy potential and are compatible with the soap-based systems, it is believed that the "iso" group is important to achieving these effects.

These polyethylene glycol diisostearates may be made by techniques described in the art such as R. G. Harry, (Revised by W. W. Myddleton) *COSMETIC MATERIALS—Their Origins, Characteristics, Uses and Dermatological Action*, Volume Two, (Chemical Publishing Co., Inc., 1963), for example at pages 354–356. Some of these materials may be obtained from companies specializing in such products such as the PEG-90 Diisostearate product from Scher Chemical Inc., Clifton, N.J.

The base composition according to the present invention can be in the form of a soft gel, hard stick, soft solid or cream (especially a gel composition) and contains a conventional soap gelling agent. Such soap gelling agents include those selected from the group consisting of conventional soap-gelled base formulations. The base gel compositions gelled using a soap gelling agent for depositing the active ingredient normally include as major components a mixture of from, for example, 3 to about 10% by weight (of the total weight of the composition) of an alkali metal salt of a fatty acid containing primarily, for example, 12–22, especially 12 to 18 carbon atoms (for example, sodium stearate or sodium palmitate soap), and a suitable solvent in which the soap is soluble, for example, water, organic solvents (such as lower monohydric alcohols and/or glycols), or mixtures thereof. The product forms described above (sticks, gels, soft solids, creams) may be formulated as known in the art, depending, for example, on the amount of gelling agent utilized. For example, the stick is formed by pouring a mixture of the various components into a suitably shaped mold and permitting the composition to gel and cool, thereby hardening the composition.

Examples of products included in this invention include:
(a) sticks made with 5–80% water and at least 3% of a soap gelling agent;
(b) soft solids made with 5–88% water and 0.001–3% of a soap gelling agent.

Other examples of soap gelled systems include glycerin soaps. Particular examples of such glycerin soap compositions may include the gelling agent in an amount of 12–15% based on the total weight of the final composition and the material gelled with the gelling agent at a level of 40–85% based on the total weight of the final composition. The gel-forming agent used in the present invention can be one of those conventionally used in the art. A preferred gel-forming agent, appropriate in deodorant gel compositions, is a soap which is a metal salt of one or more fatty acids having a chain length of 12–22 carbon atoms. Preferred are the alkali metal, for example, sodium or potassium, salts of fatty acids containing 12–22 carbon atoms. The fatty acid portion of the soap is preferably a relatively pure saturated or unsaturated $C_{12}$ to $C_{22}$ acid including myristic, palmitic, stearic, oleic, linoleic, linolenic and margaric acids, as well as mixtures thereof. Naturally occurring sources of such acids include coconut oil, beef tallow, lanolin, fish oil, palm oil, peanut oil and the like.

Thus, preferred soaps include sodium stearate, sodium palmitate, potassium stearate, potassium palmitate, potassium myristate and sodium myristate, with sodium stearate being most preferred. Generally, the sodium soaps are used to formulate sticks, with stick hardness being directly proportional to the level of sodium stearate. The potassium soaps may be used to form soft gels.

The most preferred soap is sodium stearate, which in actuality is a mixture of sodium salts of fatty acids have $C_{12}$ to $C_{22}$ carbon chain lengths in various ratios. As for various soap gelling agents which can be utilized according to the present invention, see U.S. Pat. No. 5,424,070, the contents of which are incorporated herein by reference for their identification of various soap gelling agents.

The soap may be present in the composition at a level of from about 2–12% by weight, more preferably 3–10% by weight, most preferably from about 5–9% by weight, of the total weight of the composition. For sticks a minimum amount of 3% gelling agent (such a sodium stearate) is preferred. Other soap based gelled systems may be created which maintain a clear appearance using this invention.

By utilizing the polyethylene glycol diisostearate component in the base gel composition as in the present invention, the composition is considerably less irritating to the skin than conventional soap-based gel formulations.

An important feature of this invention is that the cosmetic compositions are more stable, for example, as compared to compositions containing other anti-irritants. For example, while a material such as diisostearyl dimerate is able to produce a microemulsion formula having reduced irritation, it is not able to exhibit sufficient compatibility with soap-based gel systems to yield a stable product.

Glycols typically used in these systems can affect appearance, irritancy and solubility of additional key ingredients. This invention enables the user to formulate over a wide range of molecular weights for glycols and still achieve desirable results. For example, glycols such as one or more members selected from the group consisting of propylene glycol, dipropylene glycol, 2-methyl 1,3 propanediol (also called MPDiol), tripropylene glycol, tetrapropylene glycol, and other polypropylene glycols (also called PPG's) having Formula I: $H(OCH_2—CH(CH_3))_n—OH$ (Formula I) where n is a number from 5–50, for example, n may be selected from the group consisting of 9, 12, 15, 17, 20, 26, 30, 32 and 34.

Lower molecular weight glycols (76 to 134 g/mole) may be used to form clear deodorant products. While higher molecular weight polyols (for example glycols) (for example, 135 to 2918 g/mole) lower the volatility of the solvent component and can be used to make more opaque products with longer lasting fragrance.

The base gel composition according to the present invention which acts as a vehicle for depositing a cosmetically active ingredient on the skin, can also include water, as in conventional gel compositions. Water can be included in the composition in amounts up to 88% by weight, of the total weight of the composition. Preferably, where the compositions according to the present invention contain water, the water is included in the composition in an amount in a range from about 5% by weight, to about 88% by weight, water, of the total weight of the composition. Preferred water-containing compositions contain from about 5% to about 40% by weight water, more preferably from about 10% to 30% by weight water and, more particularly, no more than 22% water (such as in the range of 10–22% water) based on the total weight of the composition. The water serves as a diluent for the ingredients in the composition and may assist in solubilization of actives or other ingredients added to the compositions, as well as assist in gelation of the composition and in formation of a more transparent gel.

Other optional ingredients may also be included such as fragrances, surfactants, emollient, anti-bacterials, a cosmetically active ingredient, coloring agents, clarifying or opacifying agents, absorbents, silicones and polymers.

The cosmetically active ingredient incorporated in the base gel composition, according to the present invention, can be those conventionally known in the art, and include (but are not limited to) antiperspirant active agents, deodorant active agents, insect repellents, sunscreens, etc., as discussed previously and as described in U.S. Pat. No. 4,322,400, the contents of which are incorporation herein by reference in their entirety. Other actives include fungicides, analgesics, emollients, ultraviolet absorbers or talc, etc. Other active ingredients are disclosed in U.S. Pat. No. 4,382,079 to Marschner, the contents of which are also incorporated herein by reference for their description of such ingredients.

Depending on identity and function, the actives may be added to the gel compositions at various levels, that is, in sufficient amounts to achieve the desired effect; for example, deodorant actives may be added to soap-based gel compositions at levels up to about 3% by weight of the active ingredient, of the total weight of the composition. The active ingredient must be stable in the environment of the gel composition. For example, where the gelling agent is a soap such as sodium stearate, any active ingredient must be stable in the alkali environment provided by the sodium stearate/glycol or sodium stearate/water/glycol vehicle.

By rubbing the cosmetic gel composition according to the present invention on the skin, the cosmetically active ingredient incorporated therein can be deposited in a film of the base gel composition on the skin, while achieving a film having reduced skin irritation potential.

If it is desired to form cosmetic products with an antiperspirant claim and/or action, an antiperspirant active material should also be included in the composition. Various antiperspirant active materials that can be utilized according to the present invention include conventional aluminum and aluminum/zirconium salts, as well as aluminum/zirconium salts complexed with a neutral amino acid such as glycine, as known in the art. See each of EPA No. 512,770 A1 and PCT No. WO 92/19221, the contents of each of which are incorporated herein by reference in their entirety, for disclosure of antiperspirant active materials. The antiperspirant active materials disclosed therein, including the acidic antiperspirant materials, can be incorporated in the compositions of the present invention. Suitable materials include (but are not limited to) aluminum chlorohydroxide, aluminum chloride, aluminum sesquichlorohydroxide, zirconyl hydroxychloride, and aluminum chlorohydrol-propylene glycol complex. These include, by way of example (and not of a limiting nature), aluminum chlorohydrate, aluminum chloride, aluminum sesquichlorohydrate, zirconyl hydroxychloride, aluminum zirconium glycine complex (for example, aluminum zirconium trichlorohydrex gly, aluminum zirconium pentachlorohydrex gly, aluminum zirconium tetrachlorohydrex gly and aluminum zirconium octochlorohydrex gly), aluminum chlorohydrex PG, aluminum chlorohydrex PEG, aluminum dichlorohydrex PG, and aluminum dichlorohydrex PEG. The aluminum-containing materials can be commonly referred to as antiperspirant active aluminum salts. Generally, the foregoing metal antiperspirant active materials are antiperspirant active metal salts. In the embodiments which are antiperspirant compositions according to the present invention, such compositions need not include aluminum-containing metal salts, and can include other antiperspirant active materials, including other antiperspirant active metal salts. Generally, Category I active antiperspirant ingredients listed in the Food and Drug Administration's Monograph on antiperspirant drugs for over-the-counter human use can be used. In addition, any new drug, not listed in the Monograph, such as aluminum nitratohydrate and its combination with zirconyl hydroxychlorides and nitrates, or aluminum-stannous chlorohydrates, can be incorporated as an antiperspirant active ingredient in antiperspirant compositions according to the present invention. Preferred antiperspirant actives that can be incorporated in the compositions of the present invention include the enhanced efficacy aluminum salts and the enhanced efficacy zirconium/aluminum salt-glycine materials, having enhanced efficacy due to improved molecular distribution, known in the art and discussed, for example, in PCT No. WO 92/19221, the contents of which are incorporated by reference in their entirety herein.

The amount of antiperspirant active material incorporated in the stick composition of the present invention is, preferably, an antiperspirant effective amount; that is, an amount to reduce the flow of perspiration from the location (for example, axillary region of a human) to which the antiperspirant is applied. For an antiperspirant product an amount of 5.0–25%, particularly 5–20%, even more particularly 7–15%, and especially 7–12% by weight based on the total weight of this composition may be used. The amount of antiperspirant material utilized is dependent on the efficacy of the specific antiperspirant material, as well as a maximum amount which avoids a reduction in clarity of the final product.

For deodorant products a lower level of antiperspirant active can be used such as a level of from 0.5–20%, particularly 0.5–7.0%, and more particularly 0.5–5.0% by weight based on the entire weight of the composition is used. As is known to those skilled in the art, the use of antimicrobials and/or fragrances can also be included in efficacious amounts in deodorant products to reduce or mask odor.

For embodiments of the invention which contain an antiperspirant (either at a level denominated "deodorant" or at a level denominated "antiperspirant") it is preferred that a stabilizing agent also be included. Examples of suitable stabilizing agents include cosmetically acceptable alkali metal salts, bases, amines and other nitrogen containing compounds, particularly guanidine carbonate (described in U.S. Pat. No. 5,490,979 and assigned to the same assignee as this application).

While it is contemplated that the cosmetic compositions of this invention are especially useful as deodorants, for example with the use of an antibacterial, a fragrance or lower amounts of an antiperspirant actives, these compositions can also be formulated into antiperspirants by using effective levels of antiperspirant actives as noted above.

Known bacteriostats useful in the compositions include bacteriostatic quaternary ammonium compounds (cetyltrimethylammonium bromide), 2-amino-2-methyl-1-propanol (AMP), cetyl pyridinium chloride, 2, 4, 4'-trichloro-2'-hydroxydiphenylether (Triclosan), N-(4-chlorophenyl)-N'-(3,4-dichlorophenyl)urea (Triclocarban) and various zinc salts (for example, zinc ricinoleate). The bacteriostat can, illustratively, be included in the composition in an amount of 0.01–1.0% by weight, of the total weight of the composition. Triclosan, can illustratively be included in an amount of from 0.01% to about 0.5% by weight, of the total weight of the composition.

Emollients are cosmetic ingredients that help to maintain the soft, smooth, supple and pliable appearance of skin. They function by their ability to remain on the skin, to act as lubricants in reducing flaking and irritation. They increase the water content of the top layer of the skin providing moisturization as well. The emollients may also be included, especially those selected from the group consisting of:

(a) alkoxylated alcohols with a carbon chain length between 2–22, especially 2–20 carbons—For example, alkoxylated alcohols wherein the alcohol portion is selected from aliphatic alcohols having 2–18 and more particularly from 4 to 18 carbons, and the alkylene oxide portion is selected from the group consisting of ethylene oxide, polyoxyethylene, and polyoxypropylene having a number of alkylene units from 2–53 (and more particularly from 2 to 15 units) are especially useful. Particular examples include Laureth-4 and Isosteareth-21.

(b) polymeric ethers—for example, polyoxyethylene polyoxypropylene block polymers (for example, Poloxamer 407); polyoxypropylene-3-myristyl ether (Promyristyl PM3); polyalkylene glycol monobutyl ether (UCON lubricant 50 HB 100).

(c) alkoxylated amines—for example, Poloxamine 1307 and Poloxamine 908.

(d) alkoxylated carboxylic acids with a carbon chain length between 2–22 carbons, especially 2–20 carbons—(for example, PEG stearates having a degree of ethoxylation in the range of 40–100, such as PEG 40 stearate, PEG-90 stearate and PEG-100 stearate).

(e) diisopropyl adipate (DERMOL DIA).

(f) mixtures with ethers—for example, polyoxypropylene-3-myristyl ether (Promyristyl PM3); polyalkylene glycol monobutyl ether (UCON lubricant 50 HB 100); and diisopropyl adipate (DERMOL DIA). These emollients may be used in amounts of 0.1–5% to give a total emollient (also referred to as emollient component) addition level of 0.5–10% (total emollient being the polyalkylene glycol monobutyl ether and this additional emollient component, which itself may be one or more of the additional emollients listed here).

(g) esters and mixtures—other examples of suitable emollient materials include isostearyl isostearate, isostearyl palmitate, benzyl laurate, PEG 12 and especially alkyl benzoates such as C12–C15 linear alkyl benzoates. The non-volatile emollients can include mixtures. Examples of such mixtures include isostearyl isostearate and C12–C15 alkylbenzoate; and isostearyl benzoate and benzyl laurate.

Surfactants are surface active agents that have the ability to reduce the interfacial surface tension between immiscible solvents or liquids. They are commonly classified on the basis of their ionic characteristics, as anionic, nonionic, cationic, or amphoteric. They perform a variety of different functions, solublizing agents, suspending agents, cleansing agents, emulsifying agents, foam boosters and hydrotropes. Additionally in the present invention, applicants have found that by incorporating a surface active agent selected from the group listed above clarity of the composition is significantly improved. The resulting composition is clear or at least translucent. For example, by incorporating nonionic and/or anionic surface active agents in soap-gelled compositions, clarity of the composition is significantly increased.

Illustratively (but not limiting), anionic and nonionic surfactants, which can be utilized as clarifying agents according to this aspect of the present invention, include Poloxamine 1307, PPG-2-Ceteareth-9 and sodium laureth-13 carboxylate. Illustratively (and not limiting), the surface active agent or mixture of surface active agents can be included in the composition in an amount of from about 3% to about 10% by weight, of the total weight of the composition.

Various additional components, such as coloring agents, including dyes and pigments, fillers, fragrances, etc., can be incorporated in the gel compositions of this aspect of the present invention. Fragrances and coloring agents are those which previously have conventionally been incorporated in cosmetic sticks. Reference is made, for example, to U.S. Pat. No. 5,114,717 to Kuznitz, et al; and U.S. Pat. No. 5,380,707 to Barr, et al, the contents of each of which are incorporated herein by reference for a description of various fragrance compounds which have been incorporated in cosmetic stick compositions. This invention is not limited to use of such fragrance compounds, but can include fragrance compounds conventionally in use, either for clear or non-clear sticks. When these additional components are present, they, illustratively, are included in the composition in amounts ranging from between about 0.1% to about 3.0% by weight, of the total weight of the composition.

Various other optional components can be included in the compositions according to the present invention. For example, in addition to the glycol components, water and soap gelling agents, and, for example, in addition to the deodorant active ingredient (where the composition is a deodorant gel composition), the compositions can also include emollients, fillers, chelating agents (for example, ethylene diamine tetraacetic acid), lauramide DEA, antioxidants (for example, sodium metabisulphite), pH regulating agents and other solubilizers as conventionally known in gel formulations.

Other optional components conventionally incorporated in soap-based gels are disclosed in U.S. Pat. No. 4,504,465, the contents of which are incorporated herein by reference for their description of such components.

In one particular embodiment of the invention deodorant compositions may be made. Preferably, deodorant actives are added to these compositions in a range of from about 0.01 to about 2% by weight, more preferably from about 0.05 to about 0.75% by weight, of the total weight of the composition.

Where a deodorant active ingredient is added as the cosmetically active ingredient, the composition can be used as a deodorant gel composition. A preferred category of deodorant active ingredients are the antibacterials; the one most preferred in deodorant soap-based gel compositions according to the present invention is 2-4-4'-trichloro-2'-hydroxy diphenyl ether (Triclosan). Other antibacterial ingredients include bacteriostatic quaternary ammonium compounds such as cetyl trimethylammonium bromide, cetyl pyridinium chloride, benzethonium chloride, diisobutyl phenoxy ethoxy ethyl dimethyl benzyl ammonium chloride, N-alkylpyridinium chloride, N-cetyl pyridinium bromide, sodium N-lauroyl sarcosine, sodium N-palmetoyl sarcosine, lauroyl sarcosine, N-myristoyl glycine, potassium N-lauroyl sarcosine and stearyl trimethyl ammonium chloride. The antibacterial or bacteriostatic compounds are usually present in a range of about 0.01% to 1.0% by weight, of the total weight of the composition; preferably, 0.05%–0.5% by weight of the antibacterial or bacteriostatic compound is present.

Conventional deodorant active materials, for forming deodorant gel compositions (including deodorant gel compositions containing soap gelling agents) according to this aspect of the present invention, are disclosed in previously mentioned U.S. Pat. No. 4,322,400 and in U.S. Pat. No. 4,759,924 to Luebbe, et al. These deodorant active materials include known deoperfumes.

Additionally, deodorant compositions can be formed with lower levels of antiperspirant actives, such as in the range of 2–10%, especially 4–8% by weight based on the total weight of the composition can also be used. Such levels are below the level needed to achieve antiperspirancy, but are sufficient to have a deodorant effect.

An illustrative deodorant gel composition within the scope of this aspect of the present invention which may be made as a stick if sufficient gelling agent is used is set forth in the following. This composition is one example, and is not limiting of the present invention. The composition includes, in percent by weight of the total weight of the composition:

(a) 2%–12% by weight of a gelling agent;

(b) 10%–95% by weight of a solvent component such as glycols (for example, one or more of propylene glycol, dipropylene glycol and tripropylene glycol), which is gelled by the gelling agent;

(c) deodorant active ingredients, in an amount sufficient to have a deodorizing effect; and (d) an effective amount of an anti-irritancy agent selected from the group consisting of PEG 40–100 diisostearates, especially 0.05–10%, preferably 2.0%, and especially PEG-90 Diisostearate;

(e) 1–8%, particularly 4–6% of a surface active agent; and (f) 0–88%, particularly 5–50%, by weight water.

A more specific illustration of a deodorant gel composition of the present invention, which is not intended to be limiting of the present invention, is set forth in the following, in percent by weight of the total weight of the composition:

(a) 3%–10% of a soap that includes metal salts of at least one fatty acid having carbon chain length in the range of 12–22 carbon atoms;

(b) 0–25% by weight water, for example 5–25% water;

(c) 40%–80% by weight of solvent component comprising glycols (for example, one or more of propylene glycol, dipropylene glycol and tripropylene glycol), (d) 0–0.3% by weight of an antibacterial such as Triclosan;

(e) 0.05–10% of an anti-irritancy agent selected from the PEG diisostearates listed above, especially PEG-90 diisostearate;

(f) 1–8%, particularly 4–6% of a surface active agent; and (f) optionally 0–2.5% by weight fragrance and color.

Specific illustrative surface active agents which can be incorporated as clarifying agents according to this aspect of the present invention include Poloxamine 1307, PPG-2-Ceteareth-9 and sodium laureth-13-carboxylate. However, the nonionic and/or anionic surface active agents which can be utilized as a clarifying agent according to the present invention are not limited to the above-referred-to three surfactants. Various other known nonionic and/or anionic surface active agents can be utilized.

The nonionic and/or anionic surface active agent is included in the composition in an amount sufficient to improve clarity of the composition. Illustratively, and not limiting, this surface active agent (or mixture of surface active agents) is incorporated in the composition in an amount of about 3% to about 10% by weight, of the total weight of the composition.

Illustratively, some of the suggested emollients or surfactants can reduce clarity. An example of this is the UCON material described above.

Examples of antiperspirants formulated according to this invention include the following. Note that lower concentrations of antiperspirant active in propylene glycol will be in solution, while higher concentrations will be in dispersions. Any of the antiperspirant actives described herein can be used in these formulations.

| Ingredient | range of ingredients | preferred range |
| --- | --- | --- |
| Solvent (selected from a range of glycols having the following percentages, but provided that the total is at least 5%): | 5–88% | 60–75% |
| Propylene Glycol | 0–88% | 10–18% |
| Dipropylene Glycol | 0–35% | 25–35% |
| tripropylene Glycol | 0–88% | 16–26% |
| Propylene Glycol solution or dispersion of antiperspirant active | 1–50% (7–25% actives) | 10–20% (10–20% actives) |
| compatible gelling agent | 1–10% | 4–8% |
| emollient | 0–5% | 1–2% |
| antibacterial agent | 0.01–2.0% | 0.05–0.5% |
| anti-irritancy agent | 0.1–10% | 1–3% |
| fragrance (optional) | 0.1–10% | 1–3% |

Compositions according to the present invention can be made utilizing conventional techniques for forming gel compositions including sticks, gels, soft solids, and creams. For example, for preparing stick compositions according to the present invention, the components, in liquid (molten) form, can be mixed together and then poured into dispensing packages or molds, after which they are permitted to gel. Heating of the components to 60 degrees-90 degrees C is usually necessary in order to provide the components in liquid form for the necessary mixing. In view of processing at relatively high temperatures, it is desirable to add the fragrances at a relatively late time during mixing, as is conventional in the art, so as to avoid volatilization of the fragrances.

The gels according to the present invention are used as such products are conventionally used by the consumer. Thus, the soft gel or the stick is rubbed, for example, on the area of the body where application is desired. Illustratively, in the case of a deodorant soft gel or stick for application to the axillary area, the soft gel or stick is rubbed in the axillary area to deposit the deodorant active agent on the skin. In use the end of the stick is exposed from the conventional dispensing package and may, after use, be retracted back into the dispensing container until the next use.

In the case of a flowable gel, the consumer extrudes an appropriate amount of product from the package through slots or pores in the top of the package and applies the dispensed amount by rubbing the top of the package on the skin.

While the present invention will be described in connection with specific and preferred embodiments, it will be understood that it is not intended to limit the invention to those embodiments. To the contrary, it is intended to cover all alterations, modifications and equivalents as may be included within the spirit and scope of the invention as defined by the appended claims.

Sample examples of deodorant formulations in which this invention can be used include:

| Solid-Formulation A: | | |
|---|---|---|
| Ingredient | range of ingredients | preferred range |
| Solvent (selected from a range of glycols having the following percentages, but provided that the total is at least 5%): | 5–88% | 60–75% |
| Propylene Glycol | 0–88% | 10–18% |
| Dipropylene Glycol | 0–35% | 25–35% |
| tripropylene Glycol | 0–88% | 16–26% |
| (Optional) Propylene Glycol solution of antiperspirant active* | <10% actives | 4–6% actives |
| water | 1–50% | 10–20% |
| compatible gelling agent | 1–10% | 4–8% |
| emollient | 0–5% | 1–2% |
| antibacterial agent | 0.01–2.0% | 0.05–0.5% |
| anti-irritancy agent | 0.1–10% | 1–3% |
| fragrance (optional) | 0.1–10% | 1–3% |

| Solid-Formulation B | | |
|---|---|---|
| Ingredient | range of ingredients | preferred range |
| Solvent (selected from a range of glycols having the following percentages, but provided that the total is at least 5%): | 5–88% | 60–75% |
| Propylene Glycol | 0–88% | 10–18% |
| Dipropylene Glycol | 0–35% | 25–35% |
| tripropylene Glycol | 0–88% | 16–26% |
| (Optional) Propylene Glycol solution of antiperspirant active* | <10% actives | 4–6% actives |
| water | 1–50% | 10–20% |
| compatible gelling agent | 1–10% | 4–8% |
| emollient | 0–5% | 1–2% |
| antibacterial agent | 0.01–2.0% | 0.05–0.5% |
| anti-irritancy agent | 0.1–10% | 1–3% |
| fragrance (optional) | 0.1–10% | 1–3% |
| Soft solid | | |
| Solvent (selected from a range of glycols having the following percentages, but provided that the total is at least 5%): | 5–88% | 60–75% |
| Propylene Glycol | 0–88% | 10–18% |
| Dipropylene Glycol | 0–35% | 25–35% |
| tripropylene Glycol | 0–88% | 16–26% |
| (Optional) Propylene Glycol solution of antiperspirant active* | <10% actives | 4–6% actives |
| water | 1–50% | 10–20% |
| ethanol | 1–10% | 2–5% |
| compatible gelling agent | 1–10% | 4–8% |
| emollient | 0–10% | 3–5% |
| antibacterial agent | 0.01–2.0% | 0.05–0.5% |
| anti-irritancy agent | 0.1–10% | 1–3% |
| fragrance (optional) | 0.1–10% | 1–3% |
| Flowable gel | | |
| Solvent (selected from a range of glycols having the following percentages, but provided that the total is at least 5%): | 5–88% | 60–75% |
| Propylene Glycol | 0–88% | 10–18% |
| Dipropylene Glycol | 0–35% | 25–35% |
| tripropylene Glycol | 0–88% | 16–26% |
| (Optional) Propylene Glycol solution of antiperspirant active* | <10% actives | 4–6% actives |
| water | 1–50% | 25–40% |
| ethanol | 1–10% | 2–5% |
| compatible gelling agent | 1–10% | 4–8% |
| emollient | 0–10% | 3–5% |
| antibacterial agent | 0.01–2.0% | 0.05–0.5% |
| anti-irritancy agent | 0.1–10% | 1–3% |
| Cream | | |
| Solvent (selected from a range of glycols having the following percentages, but provided that the total is at least 5%): | 5–88% | 60–75% |
| Propylene Glycol | 0–88% | 10–18% |
| Dipropylene Glycol | 0–35% | 25–35% |
| tripropylene Glycol | 0–88% | 16–26% |
| (Optional) Propylene Glycol solution of antiperspirant active* | <10% actives | 4–6% actives |
| water | 1–50% | 40–60% |
| compatible gelling agent | 1–10% | 4–8% |
| emollient | 0–10% | 6–8% |
| surfactant(emulsifier) | 1–10% | 3–5% |
| antibacterial agent | 0.1–2.0 | 0.05–0.5% |
| anti-irritancy agent | 0.1–10% | 1–3% |
| fragrance (optional) | 0.1–10% | 1–3% |

Thus, while the description is most specific with respect to clear deodorant stick or soft gel compositions, the present invention is not limited to clear gel compositions, or to soft gel or stick compositions, or to deodorant compositions, but includes within its scope various cosmetic products, depending on the cosmetically active material incorporated in the composition.

Throughout the present disclosure, where compositions are described as including or comprising specific components or materials, it is contemplated by the inventors that compositions of the present invention also consist essentially of, or consist of, the recited components or materials. Accordingly, throughout the present disclosure any described composition of the present invention can consist essentially of, or consist of, the recited components or materials.

Throughout the present disclosure, various components of the disclosed compositions are denoted by their name in the *CTFA International Cosmetic Ingredient Dictionary* (4th Ed. 1991), the contents of which are incorporated herein by reference in their entirety.

The present invention, in one of its aspects, is directed to clear or translucent gel compositions. By clear or translucent, we mean the usual dictionary definitions of these terms. Thus, a clear gel composition, like glass, allows for ready viewing of objects behind it. A translucent gel composition, although allowing light to pass through, causes the light to be so scattered that it will be impossible to clearly identify objects behind the translucent gel. Opaque gels do not permit light to pass through. Thus, according to the present invention, there is a distinction between "clear" and "translucent" gels, and between these gels and "opaque" gels. Opaque compositions are also included.

As mentioned previously, the present invention includes within its scope (but is not limited to) "soft gels" and sticks. The stick form can be distinguished from a soft gel in that, in a stick, the formulated product can maintain its shape for extended time periods outside the package, the product not losing its shape significantly (allowing for some shrinkage due to solvent evaporation). Soft gels can be suitably packaged in containers which have the appearance of a stick, but which dispense through apertures (for example, slots or pores) on the top surface of the package.

In the cosmetics field, systems are classified as soft gels or sticks, depending on their viscosity or hardness alone; typically, it is understood that soft gels are soft, deformable products while sticks are strictly free-standing solids. For example, by rheological analysis, a commercial deodorant stick has been determined to have a plateau storage modulus $G'(\omega)$ of roughly $10^5$ Pa and a complex viscosity of $10^6$ Pa second, both at an angular frequency of 0.1 rad/sec. On the other hand, a commercial antiperspirant soft gel has been determined to have a $G'(\omega)$ value of roughly $10^3$ Pa and a complex viscosity of $10^4$ Pa second (at 0.1 rad/sec). Use of the present glycol component provides particularly good results in connection with soap-based compositions (for example, deodorant gel compositions gelled utilizing a soap gelling agent).

It has long been known that soap-based deodorant gel compositions containing sufficient soap to form a suitable gel can cause skin irritation when applied to the skin of a person. Varying degrees of irritation have been observed whether or not the liquid used to formulate the soap-gelled composition is water or a conventional alcohol such as ethanol or a glycol such as propylene glycol, although water-based compositions show considerably less irritation. For this reason, it was believed that the primary skin irritant was the soap, and that irritation could not be eliminated by simply changing the liquid formulated with the soap. However, it has been surprisingly found that the use of the polyethylene glycol Diisostearate materials described above gives rise to significantly reduced irritation when such soap-gelled compositions are applied to the skin.

The following Examples are offered as illustrative of the invention and are not to be construed as limitations thereon. In the Examples and elsewhere in the description of the invention, chemical symbols and terminology have their usual and customary meanings. Temperatures are in degrees C unless otherwise indicated. The amounts of the components are in weight percents based on the standard described; if no other standard is described then the total weight of the compositions is to be inferred. Various names of chemical components used in this application include those listed in the *CTFA International Cosmetic Ingredient Dictionary* (Cosmetics, Toiletry and Fragrance Association, Inc., $4^{th}$ ed. 1991).

EXAMPLES

Example A

General Method

Batch Making Procedures for Quantities of 100 to 2500 Grams

The solvent was weighed into a large beaker on a two-decimal-place balance. The solvent was heated to 75 degrees C on an electric hotplate with continuous stirring. The temperature was monitored with a resistance thermometer. The beaker was covered with aluminum foil to prevent heat and material loss. While the solvent was heating, Triclosan was weighed on a three-decimal-place balance and then added to the solvent. Sodium Stearate was weighed into a plastic dish, then added slowly to the solvent with continual agitation. The mixture was stirred until a clear solution was obtained. The surfactant was weighed on a two-place balance and added to the mixture while maintaining temperature and agitation. The anti-irritant was added and the mixture stirred until clear. The tetrasodium EDTA was mixed with the water, then added, allowing the temperature to decrease to 65 degrees C. Fragrance and color were weighed out and added to the preparation, and the mixture stirred an additional five minutes then poured into appropriate containers.

Examples 1–11

The method described in Example A was used to make the products shown in Examples 1–11 in Table 1 with the amount of materials listed therein. The sodium stearate is a composed of a blend of material derived from double-pressed and triple-pressed stearic acid.

TABLE 1

| Ingredient (%) | Ex. 1 | Ex. 2. | Ex. 3 | Ex. 4 | Ex. 5 | Ex. 6 | Ex. 7 | Ex. 8 | Ex. 9 | Ex. 10 | Ex. 11 |
|---|---|---|---|---|---|---|---|---|---|---|---|
| Propylene Glycol | 73.00 | 73.00 | 73.00 | 73.00 | 73.00 | 73.00 | 36.5 | | 73.00 | 73.00 | |
| Sodium Stearate | 6.00 | 6.00 | 6.00 | 6.00 | 6.00 | 6.00 | 6.00 | 6.00 | 6.00 | 6.00 | 6.00 |
| Triclosan | 0.05 | 0.05 | 0.05 | 0.050 | 0.05 | 0.05 | 0.050 | 0.050 | 0.050 | 0.050 | 0.05 |
| Sodium Laureth-13 Carboxylate | 6.00 | 6.00 | 3.000 | | 6.00 | 6.00 | 6.00 | 6.00 | 6.00 | 6.000 | 6.00 |
| Deionized Water | 13.507 | 14.947 | 17.947 | 20.947 | 14.947 | 14.947 | 14.947 | 14.947 | 14.447 | 14.447 | 14.947 |
| Fragrance | 1.40 | | | | | | | | | | |
| Coloring agent | 0.04 | | | | | | | | | | |
| Tetrasodium EDTA | 0.003 | 0.003 | 0.003 | 0.003 | 0.003 | 0.003 | 0.003 | 0.003 | 0.003 | 0.003 | 0.003 |
| Tripropylene Glycol | | | | | | | 36.5 | 36.5 | | | 73.00 |
| Dipropylene Glycol | | | | | | | | 25.55 | | | |
| PPG-9 | | | | | | | | 10.95 | | | |
| Quench-T | | | | | | | | | | 0.50 | |
| alpha-Bisabolol | | | | | | | | | | | 0.50 |
| Total | 100.000 | 100.000 | 100.000 | 100.000 | 100.000 | 100.000 | 100.000 | 100.000 | 100.000 | 100.000 | 100.000 |

Common ingredients are sodium stearate, Triclosan, tetrasodium EDTA, q.s. $H_2O$
Quench-T is an extract of kola, mate and guarana.

Examples 12–17

The method described in Example A may be used to make deodorant compositions using the ingredients listed in Table 2.

TABLE 2

| Ingredient | Ex. 12 | Ex. 13 | Ex. 14 | Ex. 15 | Ex. 16 | Ex. 17 |
|---|---|---|---|---|---|---|
| propylene glycol | 73.00 | 73.00 | 73.00 | 73.00 | 72.00 | 73.00 |
| sodium stearate | 5.00 | 6.00 | 6.00 | 6.00 | 5.50 | 7.00 |
| sodium laureth-13 carboxlate (70%) | 6.00 | 6.00 | 5.00 | 6.00 | 5.50 | 5.00 |
| PEG-90 diisostearate | 2.00 | 1.50 | 2.00 | 2.00 | 1.00 | 2.00 |
| Triclosan | 0.05 | 0.05 | 0.05 | 0.05 | 0.05 | 0.05 |
| fragrance | 1.50 | 1.50 | 1.50 | 1.50 | 1.50 | 1.50 |
| deionized water | q.s. | q.s. | q.s. | q.s. | q.s. | q.s. |
| Total | 100 | 100 | 100 | 100 | 100 | 100 |

Example B

Evaluation of Irritancy

Each of the formulations of Examples 1–11 was evaluated for its tendency to cause skin erythema using the 21-Day Cumulative Irritation Test. In this test, 0.2 g of undiluted deodorant is applied daily for 21 days (excluding weekends) to the same 2-cm square patch of skin, which is occluded between applications. Each weekday during the test period, trained personnel grade the portion of skin where the test material is applied for signs of irritation and reapply the test material. Subjects fulfill specific inclusion criteria including not pregnant or breast feeding, over 18 years old, and without medical conditions which would interfere with the test. The grading system used is as follows:

0 No visible reaction
0.5 Papular or papulovesicular response and/or dryness without erythema
1.0 Minimal/doubtful erythema
1.5 Minimal/doubtful erythema accompanied by papular or paulovesicular response and/or dryness
2.0 Definite erythema
2.5 Definite erythema, accompanied by papular or papulovesicular response and/or dryness
3.0 Definite erythema and definite edema with or without vesicles The total score is calculated by summing each individual's score on the 21 days of the test. Weekend scores are assumed to be the same as the score on the preceding Friday. The normalized score is the total score divided by the total number of readings for all subjects and multiplied by 21 (the number of readings) and by 10 (to normalize to 10 subjects). Normalized scores are analyzed using ANOVA (analysis of variance technique described in Duncan, A. J., "Analysis of Variance", *Quality Control and Industrial Statistics* (Irwin Publishers, Homewood, Ill. 1986) including the effects of subject and product. Product comparisons are made at the 5% level based on Fisher's least significant differences.

The results from testing Examples 1–11 showed reduction in normalized irritation scores in the range of 29–76%.

An additional test was performed using two commercially available products (Commercial Product #1 and Commercial Product #2) and a third product which had the formulation of Commercial Product #2 in combination with 2% PEG 90 diisostearate. Commercial Product #1 was a two-solvent stick gelled with sodium stearate and Commercial Product #2 was a propylene glycol based stick gelled with sodium stearate which product also contained an additional surfactant. The results of the comparative test are in Table 3 and use the following irritation classification scale:

| Normalized Score | Irritation Classification |
|---|---|
| 0–49 | No Significant Irritation |
| 50–199 | Slightly Irritating |
| 200–449 | Moderately Irritating |
| 450–630+ | Highly Irritating |

TABLE 3

| Product Tested | Normalized Score | Irritation Classification |
|---|---|---|
| Commercial Product #1 | 288.6 | Moderate |
| Commercial Product #2 | 202.9 | Moderate |
| Commercial Product #2 + 2% PEG-90 Diisostearate | 98.2 | Slight |
| Control irritant-0.2% Sodium Lauryl Sulfate | 431.8 | Moderate |

Differences between all three products are statistically significant.

Examples 20–32

The method of Example A was repeated with the amounts of ingredients indicated in Table 4. Fragrance was used in an amount of 1% and sufficient deionized water was added to make 100%.

TABLE 4

| Example Number | Propylene glycol | PEG-90 diisostearate | Sodium stearate | Emollient | Deionized water |
|---|---|---|---|---|---|
| 20 | 30% | 40% | 0 | 0 | 29% |
| 21 | 50% | 20% | 0 | 0 | 29% |
| 22 | 30% | 30% | 5% | 0 | 34% |
| 23 | 40% | 20% | 5% | 0 | 34% |
| 24 | 40% | 20% | 4% | 0 | 35% |
| 25 | 40% | 20% | 3% | 0 | 36% |
| 26 | 40% | 20% | 2% | 0 | 37% |
| 27 | 40% | 20% | 1% | 0 | 38% |
| 28 | 40% | 20% | 5% | 5% UCON Lubricant 50 HB | 29% |
| 29 | 40% | 20% | 5% | 10% UCON Lubricant 50 HB | 24% |
| 30 | 40% | 20% | 5% | 5% PPG-3 Myristyl ether | 29% |
| 31 | 40% | 20% | 5% | 5% Diisopropyl adipate | 29% |
| 32 | 30% | 40% | 6% | 0 | 23% |

Examples 20–32

Evaluation

Examples 20 and 21 were made without a soap gelling agent and were run as controls for the type of solid to be obtained with a soap gelling agent. Examples 22–32 were made with a soap gelling agent and, except for Examples 26 and 27, all of the compositions for Examples 22–32 formed solid opaque products. Example 23 was slightly softer in feel than a normal commercial type of deodorant stick. Example 22 was softer than Example 23 and slightly more flexible under light pressure. Example 24 formed a solid stick which was softer in feel than Examples 22 and 23 and had slight flexibility under light pressure. Example 25 was softer in feel than Example 24 and had some residual bounce under light pressure. Example 26 formed a soft gel-like structure. Example 27 was a viscous liquid. Examples 28–31 demonstrated the desirability of having a minimal amount of at least 3% sodium stearate to form a solid stick. Example 32 did form a solid stick which was softer in feel than a normal commercial deodorant stick and showed some flexibility under light pressure. For all the examples any pressure described was applied to the top of the stick.

Accordingly, through use of the present invention, a cosmetic composition (especially a gel composition such as a soft gel or stick), including deodorant gel compositions gelled utilizing a soap gelling agent, having reduced skin irritation potential, can be achieved. Moreover, such compositions having reduced skin irritation potential, yet which are at least translucent (and, in some instances, clear) can be achieved.

As is clear from the foregoing, the composition of the present invention has applicability as a composition for delivering active cosmetic ingredients to, for example, the skin of a human. The composition has various uses, depending upon the active cosmetic ingredient incorporated therein. For example, where the active cosmetic ingredient is a deodorant active ingredient (for example, an antimicrobial agent such as Triclosan, or a fragrance), the composition can be used as a deodorant composition for application to axillary regions of the human body to reduce body malodor. However, the composition of the present invention is not limited to deodorant compositions (for example, where an insect repellent, a sunscreen agent, an emollient, etc., is incorporated in the composition, the composition can be an insect repellent, a sun protection stick, a skin softener, etc.), and is not limited to application to axillary regions of the human body.

While we have shown and described several embodiments in accordance with the present invention, it is understood that the same is not limited thereto, but is susceptible to numerous changes and modifications as known to one having ordinary skill in the art, and we therefore do not wish to be limited to the details shown and described herein, but intend to cover all such modifications as are encompassed by the scope of the appended claims.

We claim:

1. A soap based gelled antiperspirant or deodorant composition comprising as an anti-irritant at least one polyethylene glycol diisostearate which has an average degree of ethoxylation of from 40–100.

2. A composition according to claim 1 wherein the amount of polyethylene glycol diisostearate in the composition is in the range of 0.05%–40.0% by weight based on the total weight of the composition.

3. A composition according to claim 2 wherein the amount of polyethylene glycol diisostearate in the composition is in the range of 1.0%–30.0% by weight based on the total weight of the composition.

4. A composition according to claim 3 wherein the amount of polyethylene glycol diisostearate in the composition is in the range of 1.0%–20.0% by weight based on the total weight of the composition.

5. A composition according to claim 4 wherein the amount of polyethylene glycol diisostearate in the composition is in the range of 1.0%–20.0% by weight based on the total weight of the composition.

6. A composition according to claim 5 wherein the amount of polyethylene glycol diisostearate in the composition is in the range of 1.0–2.5%.

7. A composition according to any one of claims 1–6 wherein the average degree of ethoxylation of the polyethylene glycol diisostearate is 80–100.

8. A composition according to any one of claims 1–6 which is a deodorant.

9. A composition according to claim 1 comprising at least one gel-forming agent which is a soap selected from the group consisting of a metal salt of one or more fatty acids having a chain length of 12–22 carbon atoms.

10. A composition according to claim 1 further comprising a compatible solvent which is a glycol.

11. A composition according to claim 10 wherein the glycol comprises at least one member selected from the group consisting of propylene glycol, dipropylene glycol, 2-methyl 1,3 propanediol, tripropylene glycol, tetrapropylene glycol, and other polypropylene glycols having Formula I:

$$H(OCH_2-CH(CH_3))_n-OH \qquad \text{Formula I}$$

where n is a number from 5–50.

12. A composition according to claim 11 wherein the glycol is propylene glycol.

13. A composition according to claim 1 comprising a base gel composition gelled using a soap gelling agent comprising 3 to about 10% by weight, of the total weight of the composition, of an alkali metal salt of a fatty acid containing 12 to 18 carbon atoms, and a compatible solvent in which the soap is soluble selected from the group consisting of water, lower monohydric alcohols, glycols and mixtures thereof.

14. A composition according to claim 1 comprising 5–40% water.

15. A composition according to claim 1 comprising: 5–88% of a solvent comprising a glycol; 1–50% water; 1–10% soap gelling agent; and 0.1–10% polyethylene glycol diisostearate with a degree of ethoxylation of 40–100.

16. A composition according to claim 1 comprising a solvent which itself comprises a mixture of two or more polyols selected from the group consisting of propylene glycol, dipropylene glycol, 2-methyl 1,3 propanediol, tripropylene glycol, tetrapropylene glycol, and other polypropylene glycols having Formula I:

$$H(OCH_2-CH(CH_3))_n-OH \qquad \text{Formula I}$$

where n is a number from 5–50.

17. A composition according to claim 15 or 16 further comprising 0.01–2.0% of an antibacterial agent.

18. A composition according to claim 1 further comprising at least one member selected from the group consisting of:

(a) antiperspirant active ingredients, (b) fragrances;

(c) antibacterial agents;

(d) anti-irritants;

(e) emollients; and (f) surfactants.

19. A composition according to claim 18 which is an antiperspirant.

20. A composition according to any one of claims 1 or 18 which contains a surfactant.

21. A composition according to claim 1 comprising, in percent by weight of the total weight of the composition:

(a) 2%–12% by weight of a gelling agent;

(b) 10%–95% by weight of a solvent component comprising one or more members selected from the group consisting of propylene glycol, dipropylene glycol and tripropylene glycol, which solvent component is gelled by the gelling agent;

(c) an effective amount of a deodorant active ingredients sufficient to have a deodorizing effect;

(d) an effective amount of an anti-irritancy agent selected from the group consisting of PEG 40–100 diisostearates;

(e) 1–8% of a surfactant; and (f) 0–88% by weight water.

22. A composition according to claim 21 wherein the anti-irritancy agent is PEG-90 diisostearate.

23. A composition according to claim 22 wherein the amount of water is in the range of 5–50%.

24. A composition according to claim 1 which is clear.

* * * * *